United States Patent [19]

Hansen

[11] 4,369,203
[45] Jan. 18, 1983

[54] ASBESTOS SURFACING PROCESS

[76] Inventor: Ronald P. Hansen, 4 Jonathon Pl., French's Forest. N.S.W., Australia

[21] Appl. No.: 273,312

[22] Filed: Jun. 15, 1981

[51] Int. Cl.³ .................. B05D 3/02; B05D 3/12; B32B 19/04
[52] U.S. Cl. .................. 427/10; 427/359; 427/369; 427/393.6; 427/407.1; 427/421; 428/443
[58] Field of Search .............. 427/365, 6, 369, 70, 427/397.6, 407.1, 421, 9, 10, 411, 412, 359; 428/443

[56] References Cited
U.S. PATENT DOCUMENTS 3,374,112  3/1968  Danon ........................ 427/10
3,463,659  8/1969  Dragoon et al. ............ 427/411 X

*Primary Examiner*—Michael R. Lusignan
*Attorney, Agent, or Firm*—Murray and Whisenhunt

[57] ABSTRACT

Process for the impregnation of asbestos or other fibrous material, comprising, as a first step, impregnating, with the application of pressure, the material with a polymeric resin binder to substantially saturate the material with binder and, as a second step, applying a polymeric resin compound comprising a polymeric resin and a filler. The process of the invention substantially prevents the escape of minute fibers of asbestos into the atmosphere, and so reduces the health hazard associated with asbestos.

10 Claims, 5 Drawing Figures er a non-flammable organic plasticiser (such as tri-dichloropropyl phosphate, chlorinated paraffin or tri-tolyl phosphate) or a humectant type plasticiser (such as a solution of sodium metasilicate containing a small quantity of polyhydric alcohol or a glycol). The preferred embodiment also provides for application of a roller 16 to assist impregnation of the binder into the material. The polymeric resin may be either a water emulsion or a solution in an appropriate solvent.
ASBESTOS SURFACING PROCESS This invention relates to a process for reducing the health hazard caused by the use of asbestos as a building material. In particular, the invention relates to a process which substantially prevents the escape of minute fibres of asbestos from the base material into the atmosphere.

Asbestos fibre has been used as a building material for acoustic and heat insulation for many years. The use of asbestos includes thermal insulation for the fire-proofing of steel, as acoustic sound absorbent material on walls and ceilings, as lagging on hot water and steam pipes and of course as asbestos-cement building sheet having many applications. Recently however the material has become recognised as a possible major health hazard through the inhalation by occupants of the buildings of dust and fibres released from the asbestos cladding.

Whilst buildings are no longer insulated with the material, the very large number of existing structures having asbestos present in some form poses a major problem.

It is appreciated that there is only a minimal health hazard from the installation and use of asbestos-cement sheet however asbestos dust fall-out is prolific from the other sources mentioned above. Some health authorities claim this fall-out is highly dangerous due to its carcinogenic effect on living tissue. Cases are known where asbestos dust from thermal insulation fitted to top-floor plant rooms of large buildings has been continually forced through the entire building via air conditioning ducts. In such cases, management is faced with the heavy cost of the closure of the building for removal and replacement of the asbestos material with a safer substitute. Not only is the replacement of the material expensive but many local government authorities will not allow the waste asbestos materials so produced to be dumped at normal waste disposal areas.

BRIEF DESCRIPTION OF THE INVENTION

My invention renders buildings having asbestos installations safe for occupation by treatment in situ. It has been found that the process can be applied with minimal inconvenience to normal use patterns since treatment can be made out of normal working hours if desired. Further, there is no problem disposing of what little waste material remains from the application process, since this contains little or no asbestos.

In accordance with the present invention therefore there is provided a process for treatment of asbestos or other fibrous materials comprising a first step of substantially saturating, with the application of pressure, the asbestos material with a binder being a polymeric resin, and a second step of applying a polymeric resin compound comprising polymeric resin and a filler.

DETAILED DESCRIPTION OF THE INVENTION

Figure 1:
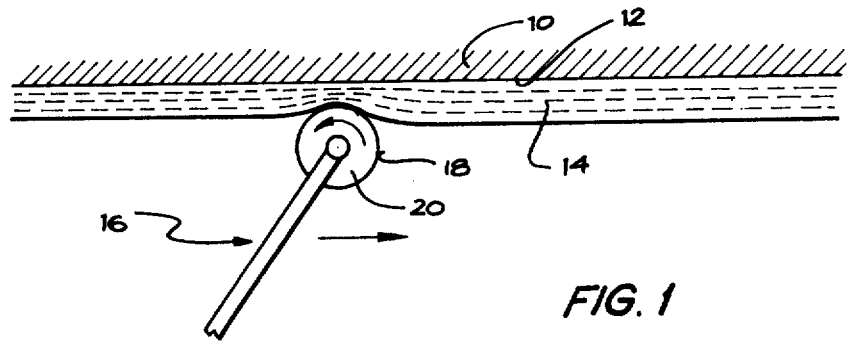
FIG. 1 illustrates the steps of rolling the fibrous asbestos to distribute the resinous material throughout.

One preferred form of this invention consists of a process enabling substantially complete impregnation of the porous asbestos or other fibrous insulation material 14 by a non-flammable binder, said binder consisting of a polymeric resin such as vinyl acetate homopolymer or a copolymer with not less than 70% by weight vinyl acetate, said polymeric resin being plasticised with either a non-flammable organic plasticiser (such as tri-dichloropropyl phosphate, chlorinated paraffin or tri-tolyl phosphate) or a humectant type plasticiser (such as a solution of sodium metasilicate containing a small quantity of polyhydric alcohol or a glycol). The preferred embodiment also provides for application of a roller 16 to assist impregnation of the binder into the material. The polymeric resin may be either a water emulsion or a solution in an appropriate solvent.

The binder solution/emulsion should have an active non-volatile binder content of between 10%–50% by weight. Further, the solution/emulsion at the working concentration as applied by the process described below should have a surface tension less than 50 dynes/cm. This will minimise the tendency of a wet roller acting on a loose fibrous surface to drag off fibers and particles by the surface tension of the liquid film between the roller surface and the wetted material.

Reduction of this drag is further achieved by a foaming action to the formulation. This leads to foam generation by the squeezing action of the roller on a porous resilient layer containing both air and the applied liquid. Such foam has less drag than a liquid film, against the separation of the roller. To maximise saturation of the layer of insulation, the viscosity of the applied binder should be as low as possible, and in any case less than 100 cps. Further, the binder is required to have a pronounced surfactant wetting action on fine fiber and dust having the surface characteristics of asbestos and fiberglass.

When dry, the film of cured binder must have the following indices of flammability as per test method of AS1530 prt 3 1976:

| Index (AS1530 pt. 3) | (a) For deep impregnation only, with finishing outer coating of (b) | (b) For final coat of exposed surface, or for deep impr. in flammable situations |
| --- | --- | --- |
| Ignitability (0–20) | less than 14 | less than 1.0 |
| Spread of flame (0–10) | 0 | 0 |
| Heat evolved (0–10) | less than 3.5 | 0 |
| Smoke developed (0–10) | less than 5.5 | 0 |

In use, my invention provides for a solution having the above properties to be applied to the asbestos substrate by a low-pressure airless spray operating in the range 15–500 psig (approximately 100 to 3500 kiloPascals). The lower pressure limit is that necessary to ensure adequate atomisation of the liquid spray as fairly large droplets for maximum penetration of the insulation, and the upper limit is determined by the necessity to avoid unnecessary disturbance of the fibrous matt and creation of consequent dust hazards in the operation. This spraying is continued to the degree of maximum feasible saturation as indicated by visual checking, with the limit indicated by runoff of excess liquid.

Then, whilst the treated layer is still wet, and before any significant loss by evaporation occurs, this embodiment of our invention provides for insulation 14 on substrate 10 to be briefly compressed by a roller 16 as shown in FIG. 1. This roller preferably incorporates a non-stick coating 18 on a firm base 20, such as a polytetrafluoroethylene coating (Teflon) over a cylinder of hard rubber or metal.

The squeezing of a resilient porous material with enough free liquid present causes movement of the liquid to penetrate entirely through the material thus compressed, wetting the entire mass of the spongey material through to the substrate interface. The roller causes up to 75% compression.

It has been found that the applied roller pressures necessary to achieve this on average asbestos or fiberglass insulation may lie between 10 and 150 kiloPascals, depending on the thickness thereof, the proportion of cementitious material originally present in the insulation when applied, and on other factors.

In certain conditions of very loosely-applied insulation, especially where there is only a small quantity of the original cementitious binder present, the surface of the insulation may be so deteriorated as to be extremely difficult to treat with the stated liquid impregnations and compress sufficiently for complete saturation. The action of squeezing/rolling may cause pulloff of the surface fibers, or even large sections of the insulation, despite the surface tension and foaming properties of the formulations described above.

Figure 2:
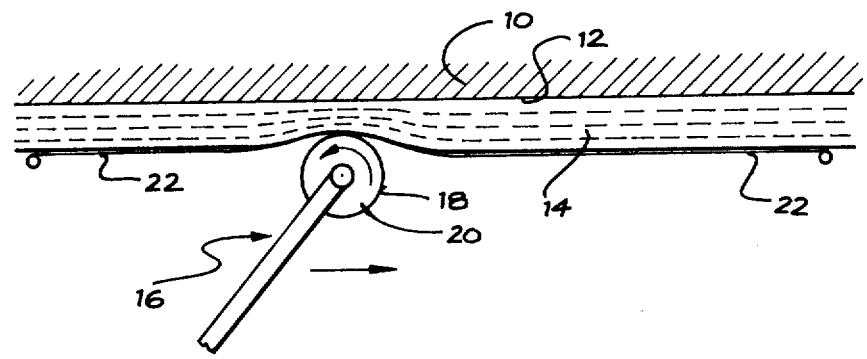
FIG. 2 illustrates rolling the fibrous material using a polyethylene sheet 22 to cut down drag on the roller.
Figure 3:
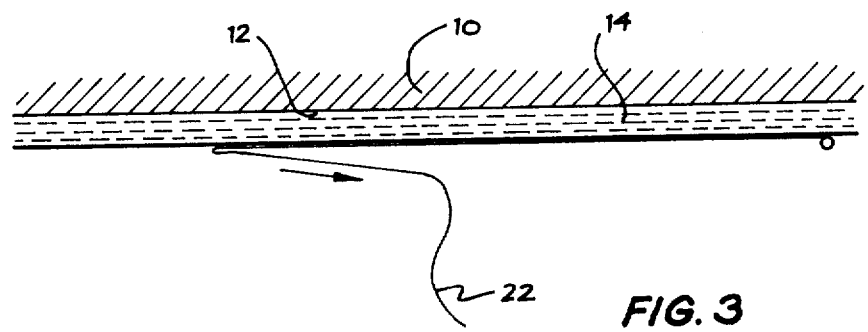
FIG. 3 illustrates removal of the polyethylene film after rolling is complete.

As illustrated in FIGS. 2 and 3, a technique for overcoming this tendency has been developed by first saturating by spraying as above, then temporarily stretching a sheet of clear plastic 22 (polythene or similar) across the area to be compressed. The roller compression is then applied over the plastic screen, which effectively prevents drag between the roller and the treated insulation material. When the insulation has been fully impregnated, the plastic sheeting is removed by a peeling action, drawing it away from the surface at an acute angle (less than 30°, as per attached sketch). The use of a transparent sheeting enables visual observation of progress of the roller squeezing action. Final checking of the degree of saturation is of course done with the electrical device outlined below.

Figure 4:
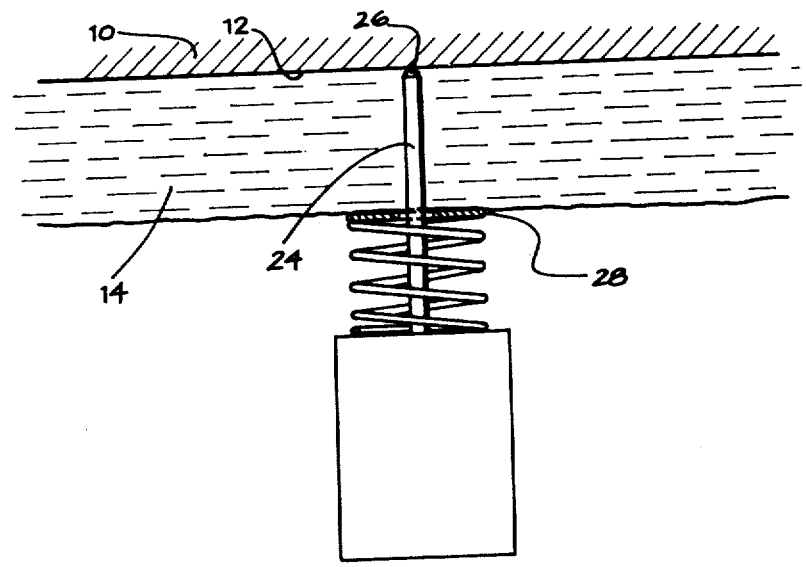
FIGS. 4 and 5 illustrate the thin metal probe used in the non-destructive testing of the degree of saturation of the asbestos base.
Figure 5:
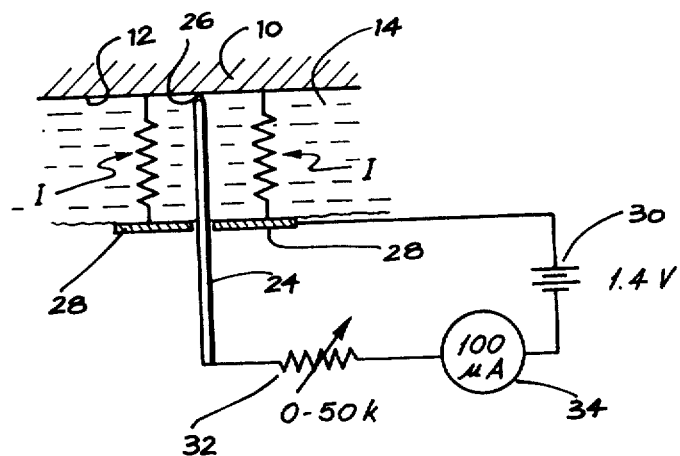

To achieve adequate stability of the applied treatment it is necessary that all the fibrous insulation material be uniformly treated with the stabiliser liquid, from the outer surface through to its interface with the substrate. Hence a method of nondestructive testing of the degree of saturation is necessary in many cases, especially where the insulation exceeds approximately 100 mm thickness. A simple method of checking this forms a part of this invention. The device employed is illustrated in FIGS. 4 and 5 and consists of a thin metal probe 24 having an insulated sleeve, which is inserted through the asbestos/fiberglass so that the tip 26 of the probe contacts the surface 12 of the substrate 10 only. A potential of between 1 and 15 volts D.C. is applied between the probe and a spring-loaded backplate electrode 28 in contact with the outer surface of the treated insulation.

The resultant current flow is of a magnitude determined by the degree of saturation of the insulation, and of its thickness. The current may be measured directly on a micro-ammeter 34, or by a transistorised device containing a trigger circuit tuned to the characteristics of the binder being applied and the insulation being treated.

In the device here preferred, an audible tone indicates whether there is a sufficiency or deficiency of the treatment liquid present. If insufficient, the spray application and rolling is repeated until there is an adequate degree of impregnation indicated in the area tested.

In general, dry insulation has an electrical conductivity nearly zero at the applied voltage. When sufficiently impregnated with the binder stated at the formulations above, the conductivity whilst still wet will be in excess of 100 microSiemens. The test device is therefore normally set for a change of audio signal at this level, although it is normally necessary to set the device for the parameters of the particular situation in each case.

The following are typical formulations suitable for the first step of our asbestos stabilising process as described above.

(A) Formula using vinyl acetate homopolymer or vinyl acetate/acrylic copolymer emulsions (by weight):

|  | | Usually | Limits |
|---|---|---|---|
| 1. | Water | 35% | |
| 2. | Dissolve ammonium bromide powder | 10% | (3% to 20%) |
| 3. | Premix nonionic surfactant @ | 1% | (0.1% to 5%) |
|  | and tri-dichloropropyl phosphate* then stir into main batch | 4% | (5% to 25% of #4) |
| 4. | Stir in unplasticised vinyl acetate** homopolymer emulsion, approx 40–50% resin content | 50% | (15% to 75%) |
| 5. | Top up with water to total batch | 100% | |

@ such as TERIC GN-9 ex ICI.
*such as FYROL FR-2 ex Stauffer Chemical Co.
**such as VINAMUL 63-076 ex A.C. Hatrick Chemical OR MACROMOL VS-2 ex Field Group Polymerics. The chemical formula of the main ingredients are as follows: - Polyvinyl acetate = generally $(CH_2:CH:C_2H_3O_2)_x$ (polymerises on drying) plasticised with - Tri-dichloropropyl phosphate = $(ClCH_3O)_3PO$ or Tritalyl phosphate $(CH_3C_6H_4O)_3PO$ (B) Formula using sodium metasilicate (by volume):

| 1. | Water | 24–1 | |
|---|---|---|---|
| 2. | Sodium metasilicate solution 40% solids (typically type N40 ex ICI) | 150–1 | (40% to 80% of total) |
| 3. | stir in glycerol OR sorbitol OR ethylene glycol | 5–1 | (1% to 10% of #2) |
| 4. | stir in nonionic surfactant typically ICI Teric GN-9 | 1% | (0.1% to 5% of total batch) |
| 5. | top up with water to batch total | 200 | liters |

The chemical formula of the main ingredients are as follows: - Sodium metasilicate (generally) $(Na_2O)_x(SiO_2)_y.nH_2O$ typically in this application $(Na_2SiO_3.5H_2O)$ (reversible) plasticised with one of the following - polyhydric alcohol (glycerol) $CHOH(CH_2OH)_2$ OR (sorbitol)
$C_6H_8(OH)_6$ OR
ethylene glycol   $CH_2OH.CH_2OH$ OR
diethylene glycol   $CH_2OH.CH_2.OCH_2.CH_2OH$ The tridichloropropyl phosphate of (A) above, and the polyhydric alcohols of (B) (for which certain ethylene glycols may be substituted) are included for the purpose of flexibility of the resulting cured adhesive bond. The unplasticised resin or raw sodium metasilicate is very brittle when dried, and such embrittlement would allow generation of dust if disturbed. The inclusion of such plasticisers gives a degree of flexibility to the film. However, plasticisers normally used for vinyl acetates and acrylics are unsuitable for this particular purpose, due to their inherent flammability. Since the insulation being treated is nearly always present as a fireproofing medium, the applied anti-dusting treatment must not degrade the flammability rating of the insulation.

Having ensured the resin has penetrated well into the asbestos mat, the polymer is then allowed to set to an elastic consistency, preserving must of the resilience and insulating properties of the untreated matrix, but increasing the tensile strength thereof sufficient to support the second polymer treatment described herein. The polymer requires properties appropriate for bonding together asbestos fibres and for bonding said fibres to the steel, concrete or other substrate.

It has been found that the usual asbestos insulation requires a total application of diluted resin formulations as described, to result in the deposition of between 30 and 180 grams of cured resin solids, per millimeter thickness, per square meter of insulated area, for optimum impregnation as imimised dust particle emission from the surface thus treated. The optimum quantity for a particular case depends on the porosity (i.e. degree of existing compaction) of the insulation, and on the quantity present of other filling or adhesive materials used in the original application of the asbestos insulation.

Having thus increased the tensile strength of the matrix the stabilized matrix may be overlaid with a sprayed application of a further polymeric material comprising a suitable polymer resin, silica sand, pigment and a fine ground mineral, said compound having a sprayable consistency. This compound is applied to a thickness of between 2 mm and 20 mm to form a hard protective coating to provide against physical damage or abrasion of the stabilized matrix of asbestos, which would possibly cause the undesirable release of further asbestos fibre. In most applications the primary resin used in the second stage is in fact the same resin used in stage one, however other compatible resins may be used, provided they pass flammability tests AS1530 pt. 3.

The pigment is used principally for decorative purposes although it has some heat reflective function also. A fine ground mineral such as chalk, calcite or other bio-compatible mineral acts as a filler for the resin.

It is essential that the protective coating take to the asbestos matrix and thus stage two can be applied either when stage one is tacky or, provided the stage two resin is sufficiently adhesive, after the asbestos matrix has become hard. It is also important that the protective coating have a slight elastomeric property to prevent fractures. The decorative film so applied is water porous, which prevents scaling off of the film which has been a disadvantage of previous methods of application due to build up of vapour pressure within the substrate. Whilst the pores are sufficiently large to be porous to water vapour, they are on the other hand too small to allow the passage of asbestos dust.

Both resin solutions must be free of all forms of asbestos filler, vinyl chloride monomers, styrene monomers, toxic pigments and other substances known to present a health hazard.

Application of the armouring compound is carried out on quite a different principle, being designed both for minimum impact damage to the asbestos matrix and for a minimum amount of deflection, and thus wastage, of sprayed resin particles.

A further advantage over the prior art is found in this invention. In existing methods of treating asbestos insulation with materials to prevent dust and fallout, the surface is commonly sprayed with liquids such as paints, or other film-forming substances, to saturation point of the surface.

It has been found that this process frequently leads to collapse of the insulation, especially from the underside of ceilings thus treated, caused by the weight of the applied fluid in mechanically-weak layers of insulation. The additional weight causes layers of saturated insulation to fall away, during the inevitably extended period between application and hardening of the paint, resin, etc. Such paints or other liquids thus contained in a thick layer of porous material (asbestos) are effectively shielded from normal drying process of air, heat, and light, and may take many days to fully harden.

This problem is overcome by a two-stage application of the two adhesive systems described in this patent application. Asbestos insulation is first saturated with the plasticised sodium metasilicate and whilst still fully wet is additionally overtreated with the polymeric adhesive. Roller compression of the treated insulation then causes blending of the two liquids now present within the insulation.

It has been found that such blending or other contact between the two liquids results in immediate gelling of the combined system. This gelling results in immediate stiffening and increased cohesion of the treated insulation, thus substantially lessening the tendency to physical collapse under the weight of applied liquid.

It has also been found that the resin treatments described also provide a degree of protection in buildings against the occurrence of vermin in the fibrous insulation thus treated. In some situations, untreated fibrous insulation becomes infested with fleas, cockroaches or other vermin. The presence of the resin impregnation makes such infestations less likely, due to the ammoniacal and alkaline salts in the cured system.

What is claimed is:

1. A process for the in situ impregnation of asbestos material, comprising a first step of substantially saturating, with the application of pressure, the said material with a binder being a polymeric resin, and a second step of applying a polymeric resin compound comprising a polymeric resin and a filler.

2. A process as claimed in claim 1 wherein said binder is non flammable and is either a vinyl acetate homopolymer or a copolymer having not less than 70% vinyl acetate by weight.

3. A process as claimed in claim 2 wherein said binder is plasticised with either a non-flammable organic plasticiser or a humectant type plasticiser.

4. A process as claimed in any one of claims 1 to 3 wherein the said binder is applied by an airless needle jet nozzle system at a pressure between 15–500 psig.

5. A process as claimed in any one of claims 1 to 4 wherein saturation of said asbestos material is achieved by the application of a roller causing a compression in the saturated material of up to 75%.

6. A process as claimed in claim 1 wherein the polymeric resin applied in the second step consists of the binder of either claim 2 or claim 3 to which has been added a filler being a fine ground mineral.

7. A process as claimed in claim 6 wherein the polymeric resin also includes a pigment.

8. A process as claimed in any one of the proceeding claims wherein the resin applied in the second stage is porous to water vapour but not dust.

9. An electrical testing meter for use with the process of claim 1, wherein the degree of saturation through the entire thickness of asbestos material on a substrate may be tested, said material having an inner surface interfacing with said substrate and an outer surface separated from said inner surface, said meter comprising an electrode and an insulated metal probe having a tip, said insulated metal probe, in use, being inserted through said material until said tip comes into contact with said substrate and said electrode is brought into contact with said outer surface of said material, said meter generating a signal indicating the amount of current flow between said tip and said electrode in contact with said outer surface of said material upon application of a potential between 1–15 volts D.C. across said probe and said electrode.

10. A process for impregnating asbestos material, said process comprising the steps of:
(a) applying a polymeric resin binder to said asbestos material, with application of pressure to said asbestos material, to give a treated material which is substantially saturated with said polymeric resin binder, said application of pressure assisting impregnation of said binder into said material; and
(b) applying to said treated material a coating of a polymeric resin material comprising a polymeric resin and a filler.

* * * * *